(12) United States Patent
Lust et al.

(10) Patent No.: US 8,439,865 B2
(45) Date of Patent: May 14, 2013

(54) PUNCTAL PLUGS

(75) Inventors: Victor Lust, Jacksonville, FL (US); Phillip King Parnell, Sr., Jacksonville, FL (US); Vincent G. McAteer, Jacksonville, FL (US); Brian Schwam, Jacksonville, FL (US); Hassan Chaouk, Jacksonville, FL (US)

(73) Assignee: Johnson & Johnson Vision Care, Inc., Jacksonville, FL (US)

( * ) Notice: Subject to any disclaimer, the term of this patent is extended or adjusted under 35 U.S.C. 154(b) by 0 days.

(21) Appl. No.: 12/749,043

(22) Filed: Mar. 29, 2010

(65) Prior Publication Data
US 2010/0256557 A1    Oct. 7, 2010

Related U.S. Application Data

(60) Provisional application No. 61/165,413, filed on Mar. 31, 2009.

(51) Int. Cl.
*A61F 9/00* (2006.01)

(52) U.S. Cl.
USPC ............ 604/93.01; 604/8; 604/104; 604/294; 128/887

(58) Field of Classification Search .............. 604/8–10, 604/38, 104, 264, 278, 285, 294, 513–514, 604/93.01; 428/422, 427–428
See application file for complete search history.

(56) References Cited

U.S. PATENT DOCUMENTS

| 5,962,548 | A | 10/1999 | Vanderlaan et al. |
| 6,020,445 | A | 2/2000 | Vanderlaan et al. |
| 6,041,785 | A * | 3/2000 | Webb ............................ 128/887 |
| 6,099,852 | A | 8/2000 | Jen |
| 6,196,993 | B1 * | 3/2001 | Cohan et al. ............... 604/891.1 |
| 6,367,929 | B1 | 4/2002 | Maiden et al. |
| 6,629,533 | B1 * | 10/2003 | Webb et al. ................... 128/887 |
| 6,822,016 | B2 | 11/2004 | McCabe et al. |
| 7,204,253 | B2 * | 4/2007 | Mendius et al. .............. 128/887 |
| 7,785,285 | B2 * | 8/2010 | Kurihashi ........................ 604/9 |
| 2006/0020248 | A1 | 1/2006 | Prescott |
| 2007/0298075 | A1 * | 12/2007 | Borgia et al. ................. 424/428 |
| 2009/0036820 | A1 * | 2/2009 | Dakin et al. ....................... 604/9 |

FOREIGN PATENT DOCUMENTS

| EP | 1629800 A1 | 3/2006 |
| WO | WO 2007149832 A2 | 12/2007 |

OTHER PUBLICATIONS

PCT Search Report PCT/US2010/029042 Date of Mailing Jul. 30, 2010.

* cited by examiner

*Primary Examiner* — Quynh-Nhu H Vu

(57) ABSTRACT

Punctal plugs for delivering therapeutic agents to the eye have a body with a portion into which the therapeutic agent is loaded and a conical anchor portion at an end of the plug.

1 Claim, 4 Drawing Sheets

PUNCTAL PLUGS

CROSS-REFERENCE TO RELATED APPLICATIONS

This is a non-provisional application which claims priority to U.S. Provisional Application 61/165,413, filed Mar. 31, 2009. The aforementioned application is incorporated in full by reference herein.

BACKGROUND OF THE INVENTION

The present invention relates to devices suitable for delivering substances to one or more of the eye, nose and throat. In particular, the invention relates to punctal plugs for delivery of at least one active agent.

Human tears are secreted by the lacrimal gland and flow across the surface of the eye to a shallow pool, known as the lacrimal lake, located where the eyelids come together at their inner ends. From there, the tears drain through small openings in each of the upper and lower eyelids, termed the superior lacrimal punctum and the inferior lacrimal punctum, respectively. From the superior and inferior puncta, the tears pass into each of the superior and inferior lacrimal canaliculus, respectively, which are duct-like pathways that lead to the lacrimal sac. The lacrimal sac is the superior, expanded portion of the nasolacrimal duct, which drains tears into the nasal system. Active agents can thus be delivered to the nose and throat through the lacrimal canaliculi, which lead into the nasolacrimal duct.

Active agents frequently are administered to the eye for the treatment of ocular diseases and disorders. Conventional means for delivering active agents to the eye involve topical application to the surface of the eye. The eye is uniquely suited to topical administration because, when properly constituted, topically applied active agents can penetrate through the cornea, conjunctiva or sclera and rise to therapeutic concentration levels inside the eye. Active agents for ocular diseases and disorders may be administered orally or by injection, but such administration routes are disadvantageous in that, in oral administration, the active agent may reach the eye in too low a concentration to have the desired pharmacological effect and their use is complicated by significant, systemic side effects, while injections pose the risk of infection, discomfort, bleeding or perforation of the globe.

The majority of ocular active agents are currently delivered topically using eye drops which, though effective for some applications, are inefficient. When a drop of liquid is added to the eye, it overfills the conjunctival sac, the pocket between the eye and the lids, causing a substantial portion of the drop to be lost due to overflow of the lid margin onto the cheek. In addition, a substantial portion of the drop that remains on the ocular surface is drained into the lacrimal puncta, diluting the concentration of the drug.

SUMMARY OF THE INVENTION

In one aspect of the invention, a punctal plug has a first end, a second end, and a lateral surface extending between the two ends; a reservoir contained within the body in which the reservoir has at least one opening, and contains an active agent-containing material with at least one active agent and the second end of the plug is an anchor having a cone shape.

In another aspect of the invention, the punctal plug has a cone shaped anchor offset from the central axis of the body of the plug.

In yet another aspect of the invention, the cone portion of the anchor of the punctal plug has the following dimensions: a base of 1.0 to 1.5 mm, an altitude of 0.3 to 1.0 mm, a radius of 0.4 to 0.85 mm, and an axis of 0 to 0.50 mm.

In yet another aspect of the invention, the punctal plug contains an active agent.

DETAILED DESCRIPTION

The punctal plugs described in this specification can be used to deliver active agents to one or both of the nasolacrimal duct and to the tear fluid of the eye. In one embodiment, the invention provides punctal plugs comprising, consisting essentially of, and consisting of: a body having a first end and a second end; a lateral surface extending between the two ends; a reservoir contained within the body wherein the reservoir comprises, consists essentially of and consists of at least one opening and contains a material that comprises, consists essentially of and consists of at least one active agent; and wherein the body is impermeable to the active agent.

Figure 1:
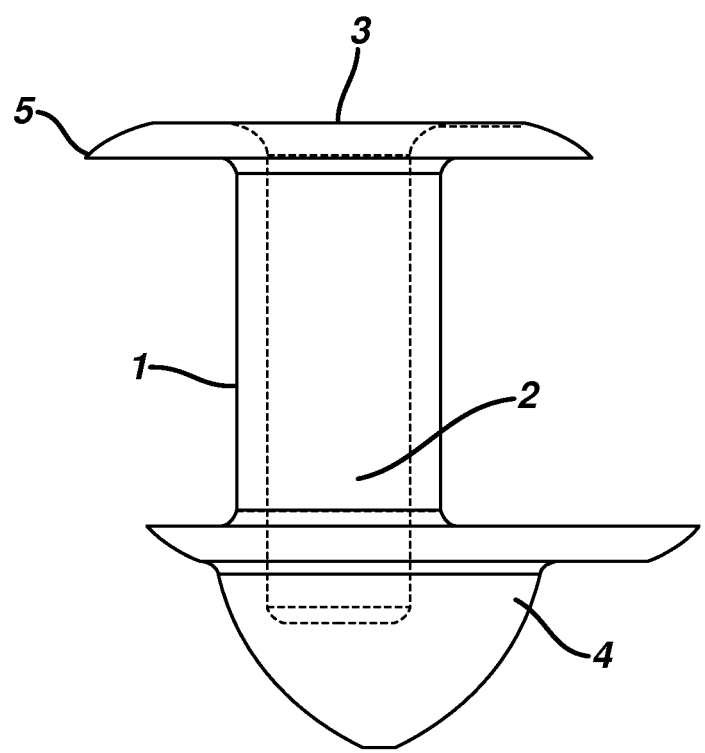
FIG. 1 is a cross sectional view of a punctal plug according to the invention having a body 1 with an enlarged segment 4 and a reservoir 2 within the body 1 that contains a polymeric material, (not shown), that contains active agent (not shown), The reservoir 2 has an opening 3 through which the active agent, is released.

Referring to FIG. 1, punctal plug body 1 as a reservoir 2 that contains at least one opening 3 and active agent (not shown) is released through opening 3, for example, when the active agent-containing material, preferably a polymeric material, dissolves, degrades, or the active agent simply diffuses or is released from the material it is associated, imbibed, or otherwise bound to, depending upon the nature of the material. The opening through which the active agent is released from the plug may be located at a first end, a second end, or both the first and second ends of the plug body or along the lateral surface thereof. Preferably, the opening is located at one or both of the first and second ends. In particular embodiments of the invention, for example as shown in FIG. 1, the punctal plug contains an enlarged segment or anchor 4 of the body 1 that is of a suitable size and shape for securing the punctal plugs in the lacrimal canaliculus.

Figure 2:
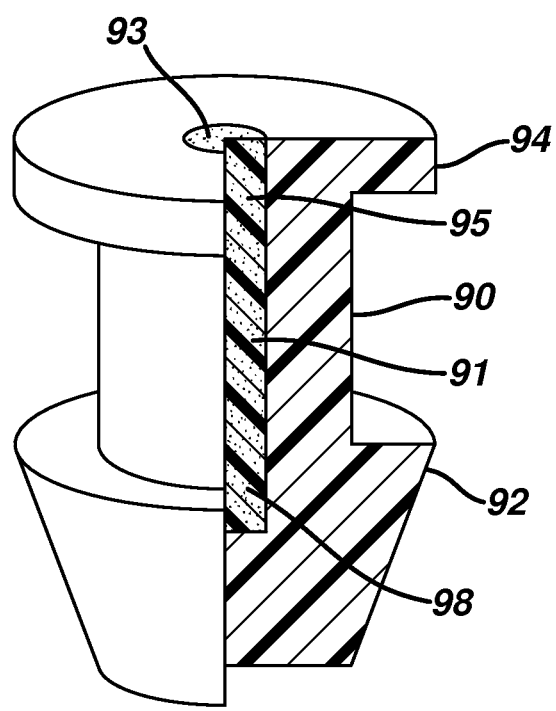
FIG. 2 is a three-dimensional view of the punctal plug depicted two-dimensionally having a body 90 with an enlarged segment 92, a reservoir 95 within the body 90 that contains a polymeric material 91 that contains active agent 98, and a collarette 94. The reservoir 95 has an opening 93 through which the active agent 98 is released.
Figure 3:
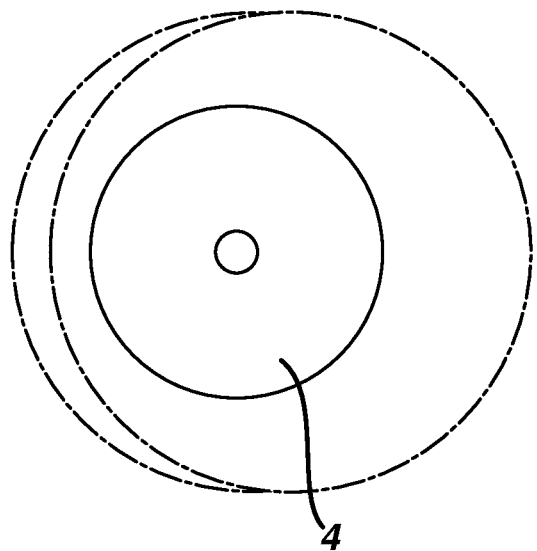
FIG. 3 is a bottom view of an anchor of a punctual plug of the invention.
Figure 4:
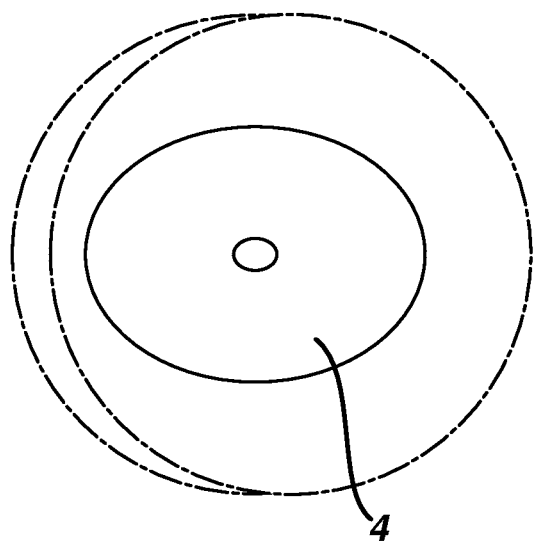
FIG. 4 is a bottom view of an anchor of a punctual plug of the invention.
Figure 5:
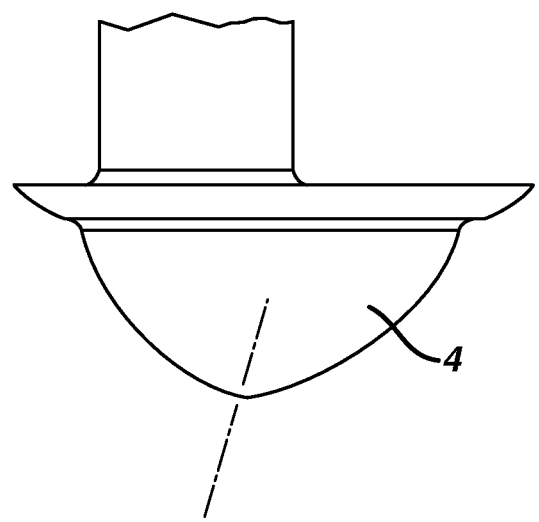
FIG. 5 is a side view of an anchor of a punctual plug of the invention showing the axis of rotation of the anchor as a dashed line.
Figure 6:
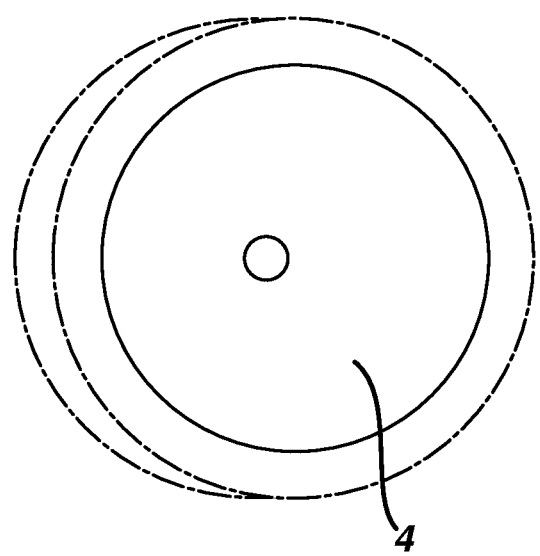
FIG. 6 is bottom view of an anchor of a punctual plug of the invention.

For delivery of an active agent into the tear fluid of the eye, a punctal plug is inserted into a lacrimal canaliculus and the active agent is released into the tear fluid of the eye. Referring to FIG. 2, for delivery into the tear fluid, a collarette 94 is preferably provided on body 90 of the punctal plug and, when the punctal plug is inserted into the lacrimal canaliculus, the collarette 94 rests on the exterior of the lacrimal punctum. For delivery of active agent into the nasolacrimal duct, a punctal plug is inserted, preferably deeply, into the lacrimal canaliculus and the active agent is released into the nasolacrimal duct.

As used herein, the term "punctal plug" refers to a device of a size and shape suitable for insertion into the inferior or superior lacrimal canaliculus of the eye through the inferior or superior lacrimal punctum.

As used herein, the term "active agent" refers to an agent capable of treating, inhibiting, or preventing a disorder or a disease. Exemplary active agents include, without limitation, pharmaceuticals and nutraceuticals. Preferred active agents are capable of treating, inhibiting, or preventing a disorder or a disease of one or more of the eye, nose and throat.

As used herein, the phrase "a material that is at least partially water-soluble" refers to a material that exhibits a level of solubility in water sufficient to result in detectable dissolution of the material upon exposure to an aqueous environment.

As used herein, the phrase "a material that is biodegradable" refers to a material that degrades to a detectable degree upon exposure to biologically active substances typically present in mammals.

As used herein, the phrase "a material that is insoluble in water" refers to a material that does not dissolve to a substantial degree upon exposure to water.

As used herein, the phrase "a material that is non-biodegradable" refers to a material that does not degrade to a substantial degree upon exposure to biologically active substances typically present in mammals.

As used herein, the phrase "body that is impermeable to active agent" refers to a body through which only an insubstantial amount of active agent can pass.

As used herein, the term "polymeric material" refers to a material made of one or more types of polymers that is capable of containing at least one active agent and releasing the active agent, for example, when the polymers dissolve or degrade, when the active agent diffuses from the polymers, or when a pro-drug is used in which the active agent is attached to the polymers and then released by being cleaved from the material.

As used herein, the term "opening" refers to an opening in the body of a punctal plug of a size and shape through which the active agent can pass. Preferably, only the active agent can pass through the opening. The opening, for example, may be a hole covered with a membrane, mesh, grid or it may be uncovered. The membrane, mesh, or grid may be one or more of porous, semi-porous, permeable, semi-permeable, and biodegradable.

As used herein, the phrase "flexible material" refers to a material that is not rigid and that substantially conforms to the surface of whatever object the material contacts.

As used herein, the phrase "the reservoir and the body are coterminous" indicates that the reservoir is substantially all of the body. A collarette can be attached to the body when the reservoir and body are coterminous, but the collarette would not considered to be part of the body.

As used herein, the phrase "refilled with active agent" refers to adding any detectable amount of active agent to the reservoir of a punctal plug.

The present invention encompasses punctal plugs for the delivery of active agents to one or both of the tear fluid of the eye and to the nasolacrimal duct. The punctal plugs preferably are inserted into the inferior lacrimal canaliculus, the superior lacrimal canaliculus, or both the inferior and superior lacrimal canaliculi. If the punctal plugs are being used to deliver active agents to the tear fluid of the eye, the punctal plugs preferably have a collarette at one end of the body. The collarette is a portion of the punctal plug that extends radially outwardly from one end of the body to a degree sufficient, and having a size and a shape, such that at least a portion of the collarette will extend beyond and be exterior to the lacrimal punctum after insertion of the punctal plug into the lacrimal canaliculus. Typically, the collarette will extend about 0.2 to about 1 mm beyond the plug body. The portion of the punctal plug without the collarette is inserted into one of the inferior lacrimal punctum or the superior lacrimal punctum. Referring to FIG. 2, enlarged segment 92 and body 90 is inserted into one of the punctum, and collarette 94 rests against the exterior of the lacrimal punctum and keeps the punctal plug from slipping down into the lacrimal canaliculus, so that contact between the punctal plug and the tear fluid of the eye is maintained.

If the punctal plugs are being used to deliver active agent to the nasolacrimal duct, the punctal plugs may not have a collarette so that they may be inserted at a sufficient depth within one or both of the lacrimal canaliculi such that the active agent is released into the lacrimal sac.

The punctal plugs of the invention each have various features and advantages. For example, certain punctal plugs have a body with a first end, a second end, and a lateral surface extending between the two ends. The lateral surface preferably has an outer diameter that is substantially circular in shape and, thus, the body preferably has a cylindrical shape. Referring again to FIG. 1, an anchor 4, is affixed to an end of the body opposite collarette 5. This anchor provides one or more surfaces in contact with the tissue in which it is inserted thus increasing the likelihood that the plug, once inserted, will remain in place. Anchor, 4 is a cone, preferably, a right circular cone with its apex directed away from body, 1. It may also take the shape of an oblique circular cone or a right or oblique elliptical cone. Preferably, anchor, 4 extends out from the end of the body from between 0 and 0.4 mm and most preferably from 0 to 0.1 mm. Anchor 4 may be fashioned in a geometry that is a combination of a cone and another shape such as a washer shape atop the cone. When this arrangement is used the washer portion (a cylinder slice with a diameter greater than that of body) atop the conical portion of the anchor may extend from 0.26 mm to 1.09 mm beyond the base of the cone portion. The anchor can be affixed by glue, welding, adhesive, or any other convenient method but it is most preferred that is formed as part of the molding process though it may be co-molded or over-molded. Preferred dimensions of the cone portion that makes a part of the anchor (in the case of a combination geometry) or the entirety of the anchor are as follows: base of 1.0 to 1.5 mm, altitude of 0.3 to 1.0 mm, radius of 0.4 to 0.85 mm, and axis of 0 to 0.50 mm. It is most preferred that the anchor is offset from the transverse axis of the body 0.20 mm. Preferably, the amount of offset is 0.085 to 0.130 mm from the center of the base of the cone of the anchor (or up to 58% of the distance from the center to the perimeter of the base of the cone). The collarette, 6 may also be off-center from this axis. A portion of the lateral surface of certain of the punctal plugs preferably has an outer diameter that is greater than the outer diameter of the remainder of the lateral surface. With reference to FIG. 2, the enlarged portion 92 of the lateral surface anchors or secures the punctal plugs in the lacrimal canaliculus. The enlarged portion can be any size or shape, and can be present on any part of the lateral surface, so long as the enlarged portion at least partially anchors the punctal plug in the lacrimal canaliculus. Preferably, the enlarged portion is at one end of the plug. Conveniently, the enlarged portion may take the shape of an inverted triangle having a flattened apex, as shown in FIG. 2, may have an untapered, body rounded at the end, or may have a tapered shape at one end with a rounded point. One ordinarily skilled in the art will recognize that any of a wide variety of shapes are possible.

The body, 90, of the punctal plugs of the invention may take any shape and size, Preferably; the body is in the shape of an elongated cylinder. The body will be about 0.8 to about 5 mm in length, preferably about 1.2 to about 2.5 mm in length. The width of the body will be about 0.2 to about 3, preferably 0.3 to about 1.5 mm.

The body of the plug may be wholly or partially transparent or opaque. Optionally, the body may include a tint or pigment that makes the plug easier to see when it is placed in a punctum.

The body of the punctal plugs may be made of any suitable biocompatible material including, without limitation, silicone, silicone blends, silicone co-polymers, such as, for example, hydrophilic monomers of polyhydroxyethylmethacrylate ("pHEMA"), polyethylene glycol, polyvinylpyrrolidone, and glycerol, and silicone hydrogel polymers such as, for example, those described in U.S. Pat. Nos. 5,962,548, 6,020,445, 6,099,852, 6,367,929, and 6,822,016, incorporated herein in their entireties by reference. Other suitable biocompatible materials include, for example: polyurethane; polymethylmethacrylate; poly(ethylene glycol); poly(ethylene oxide); polypropylene glycol); poly(vinyl alcohol); poly(hydroxyethyl methacrylate); poly(vinylpyrrolidone) ("PVP"); polyacrylic acid; poly(ethyloxazoline); poly(dimethyl acrylamide); phospholipids, such as, for example, phosphoryl choline derivatives; polysulfobetains; acrylic esters, polysaccharides and carbohydrates, such as, for example, hyaluronic acid, dextran, hydroxyethyl cellulose, hydroxyl propyl cellulose, gellan gum, guar gum, heparan sulfate, chondritin sulfate, heparin, and alginate; proteins such as, for example, gelatin, collagen, albumin, and ovalbumin; polyamino acids; fluorinated polymers, such as, for example, polytetrafluoroethylene ("PTFE"), polyvinylidene fluoride ("PVDF"), and teflon; polypropylene; polyethylene; nylon; poly/ethylvinyl acetate ("EVA"); poly/caprolactone; and poly/ethylene vinyl alcohol ("EVOH").

The surface of the plug body may be wholly or partially coated. The coating may provide one or more of lubriciousness to aid insertion, muco-adhesiveness to improve tissue compatibility, and texture to aid in anchoring the plug within the punctum. Examples of suitable coatings include, without limitation, gelatin, collagen, hydroxyethyl methacrylate, PVP, PEG, heparin, chondroitin sulphate, hyaluronic acid, synthetic and natural proteins, and polysaccharides, thiomers, thiolated derivatives of polyacrylic acid and chitosan, polyacrylic acid, carboxymethyl cellulose and the like and combinations thereof.

Certain embodiments of the punctal plugs of the invention have a body made of a flexible material that conforms to the shape of whatever it contacts. Optionally, the plug may have a collarette formed of either a less flexible material than that of the body or material that too conforms to the shape of whatever it contacts. When a punctal plug having both a flexible body and a less flexible collarette is inserted into the lacrimal canaliculus, the collarette rests on the exterior of the lacrimal punctum and the body of the punctal plug conforms to the shape of the lacrimal canaliculus. The reservoir and the body of such punctal plugs are preferably coterminous. That is, the reservoir of such punctal plugs preferably make up the entirety of the body, except for the collarette.

In embodiments in which one or both of a flexible body and collarette are used, the flexible body and flexible collarette can be made of materials that include, without limitation, nylon, polyethylene terephthalate ("PET"), polybutlylene terephthalate ("PBT"), polyethylene, polyurethane, silicone, PTFE, PVDF, and polyolefins. Punctal plugs made of nylon, PET, PBT, polyethylene, PVDF, or polyolefins are typically manufactured for example and without limitation, extrusion, injection molding, or thermoforming. Punctal plugs made of latex, polyurethane, silicone, or PTFE are typically manufactured using solution casting processes.

The punctal plugs of the invention contain a reservoir within the body, and the reservoir contains an active agent-containing material. The material may be any material that is compatible with the active agent or agents to be delivered by the plug and is capable of releasing the active agent in the desired manner, for example by dissolving or degrading of the material or diffusion of the active agent from the material. Any number of material may be used as the active agent-containing material including, without limitation, polymeric materials, both naturally occurring and synthetic, non-polymeric materials including, without limitation, glasses and clays, organic materials, inorganic materials including, without limitation, porous ceramics, lipids, waxes and the like and combinations thereof. Preferably, the active agent containing-material is a polymeric material, in which at least one active agent is disposed on, dispersed throughout, or otherwise contained. The body is preferably impermeable to the active agent, and the reservoir has at least one opening through which the active agent is released.

The body has one or more openings communicating with the reservoir at a first end, as shown in FIG. 2, a second end (not shown), or at another location on the body. In particular embodiments of the invention, when such punctal plugs are inserted into the lacrimal canaliculus and have opening at the end of the body facing the eye, the active agent is released into the tear fluid of the eye. Alternatively, if the plug has an opening in the end of the body facing the nasolacrimal duct, the active agent is released into the nasolacrimal duct. In those embodiments in which the plug has opening at the end of the body facing the eye and another opening at the end of the body facing the nasolacrimal duct, the active agent is released into both the tear fluid of the eye and the nasolacrimal duct. For those punctal plugs with a collarette, the opening of such punctal plugs is preferably located within the collarette, preferably the central portion of the collarette. When such punctal plugs are inserted into the lacrimal canaliculus, the opening faces the eye, and the active agent is released into the tear fluid of the eye.

The size of the opening will be from about 0.05 mm to about 2.5 mm and preferably about 0.15 mm to about 0.8 mm. Instead of one large opening at any one location, multiple small openings may be used.

Processes for manufacturing the punctal plugs useful in the invention are well known. Typically, the plugs are manufactured by injection molding, cast molding, transfer molding or the like. Preferably, the reservoir is filled with one or both of at least one active agent and the active agent-containing material subsequent to the manufacture of the plug. Additionally, one or more excipients may be combined with the active agent alone or in combination with the polymeric material.

Depending upon the active agent-containing material selected, the active agent can be released from the material almost immediately, or the active agent can be released in a sustained manner over a desired period of time. For example, a polymeric material may be used that is composed of one or more polymers that are at least partially soluble in water. When such a polymeric material is exposed to the aqueous environment of the lacrimal canaliculus or the tear fluid, it preferably will dissolve and release the active agent as it dissolves. The solubility in water of the one or more polymers from which the polymeric material is made typically will be directly proportional to its rate of dissolution. Suitable polymers that are at least partially soluble in water include, without limitation, poly(ethylene glycol); poly(ethylene oxide); poly(propylene glycol); poly(vinyl alcohol); poly(hydroxyethyl methacrylate); poly(vinylpyrrolidone); polyacrylic acid; poly(ethyloxazoline); poly(dimethyl acrylamide); phosolipids, such as, for example, phosphoryl choline derivatives; polysulfobetains; polysaccharides and carbohydrates, including, without limitation, hyaluronic acid, dextran, hydroxyethyl cellulose, hydroxyl propyl cellulose, gellan gum, guar gum, heparan sulfate, chondritin sulfate, heparin, and alginate; proteins such as, for example, gelatin, collagen, albumin, and ovalbumin; and polyamino acids. The polymeric materials in this list can typically be copolymerized or blended with one or both of hydrophobic polymers and monomers.

As an alternative, a non-polymeric material including, without limitation, a lipid, wax, or inorganic material may be used. Suitable non-polymeric materials include, without limitation, lanolin, paraffin, sorbates, lecithin, vitamin A, D, and E, glycerine, sorbitol, mannitol, stearates, fatty acids, lutein, zeaxanthin, taurine, glutathione and the like.

Alternatively, the active agent-containing material can be one or more biodegradable polymers that partially or wholly chemically degrade upon exposure to, for example, biologically active substances typically present in mammals. The biodegradable materials are preferably hydrolyzable under in vivo conditions. Biodegradation may occur more slowly than dissolution, and the material can thus compose one or more biodegradable polymers if slower, more sustained release of the active agent is desired.

Suitable biodegradable polymers include, without limitation, polymers and oligomers of glycolide, lactide, lactones, and other hydroxy acids, and other biologically degradable polymers that yield materials that are non-toxic or present as normal metabolites in the body. Preferred poly(alpha-hydroxy acids) are poly(glycolic acid), poly(2-dioxanone); poly (DL-lactic acid) and poly(L-lactic acid). Other useful polymers include poly(amino acids), polycarbonates, poly (anhydrides), poly(orthoesters), poly(phosphazines) and poly(phosphoesters). Polylactones including, without limitation, poly(epsilon-caprolactone), poly(delta-caprolactone), poly(delta-valerolactone) and poly(gamma-butyrolactone are also useful, as are chitosan, alginates, collagen, and gelatin. In particular aspects of the invention, the polymeric material the contains the active agent can comprise a mixture of one or more dissolvable and bio-degradable polymers.

In a preferred embodiment, the active agent-containing material is a polymeric material that is combined with at least one active agent to form one or more fiber or fiber-like structures, the dimensions of which may be substantially the dimensions of the reservoir or smaller than such dimensions, and one or more of the fibers or fiber-like structures are inserted into the reservoir through the opening in the plug body. The fibers or fiber-like structures may be of a size and a shape suitable for insertion into the opening and may be about 0.5 to about 5 mm in length and 0.05 to about 2 mm in diameter. If only one fiber or fiber-like structure is used, preferably, the dimensions of the fiber are such that the fiber fits securely into the reservoir and remains in the reservoir when the plug is in use in a wearer's punctum. Thus, the fiber can be symmetrical or asymmetrical, depending upon the shape of the reservoir. The internal walls of the reservoir may be substantially smooth or may include features that aid in maintaining the fiber within the reservoir including, without limitation, surfaces with grooves, indentations, roughness or the like in the interior walls.

Alternatively, the fiber containing the active agent or agents may be formed and the plug cast around the fiber. As yet another alternative, the fiber and active agent may be dosed or nano dosed into the plug reservoir as a melt and allowed to solidify. As still another alternative, the polymer and active agent may be introduced as a solution. The solution may contain monomers, pre-polymers and the like suitable for cross-linking via one or more of irradiation, redox, and thermal radical polymerization. As yet another alternative, the fiber may simply be soaked in the active agent before or after insertion in the plug, or it may be bound throughout the silicone or EVA plug.

Preferably the fiber or fiber-like structures are composed of a polymeric material and more preferably a polymeric material that is polycaprolactone, still more preferably poly(epsilon-caprolactone), and ethylene vinyl acetate of molecular weights between about 10,000 and 80,0000. About 0 to about 100 weight percent polycaprolactone and about 100 to about 0 weight percent of the ethylene vinyl acetate are used based on the total weight of the polymeric material and, preferably, about 50% each of polycaprolactone and ethylene vinyl acetate is used. The polymeric material used is preferably greater than about 99% pure and the active agent is preferably greater than about 97% pure. One of ordinary skill in the art will recognize that in compounding, the conditions under which compounding is carried out will need to take into account the characteristics of the active agent to ensure that the active agents do not become degraded by the process. The polycaprolactone and ethylene vinyl acetate preferably are combined with the desired active agent or agents, microcompounded, and then extruded as a fiber. The fibers are then cut to the desired length and inserted into the reservoir through one or more plug openings.

The amount of active agent used in the plugs of the invention will depend upon the active agent or agents selected, the desired doses to be delivered via the punctal plug, the desired release rate, and the melting points of the active agent and active agent-containing material. Preferably, the amount used is a therapeutically effective amount meaning an amount effective to achieve the desired treatment, inhibitory, or prevention effect. Typically, amounts of about 0.05 to about 8,000 micrograms of active agents may be used.

In certain aspects of the invention, the reservoir can be refilled with a material after substantially all of the active agent-containing material has dissolved or degraded and the active agent is released. For example, the new active agent-containing material can be the same as, or different from, the previous polymeric material, and can contain at least one active agent that is the same as, or different from the previous active agent. Certain punctal plugs used for particular applications can preferably be refilled with a material while the punctal plugs remain inserted in the lacrimal canaliculus, while other punctal plugs are typically removed from the lacrimal canaliculus, a new material is added, and the punctal plugs are then reinserted into the lacrimal canaliculus.

When the active agent-containing material is combined with the active agent, the material may also contain one or more materials that are insoluble in water and non-biodegradable, but from which the active agent can diffuse. For example, if the material is a polymeric material, the material may be composed of one or more polymers that are insoluble in water and non-biodegradable. Suitable polymers of this type include, for example, cross-liked polymers, such as, for example, cross-linked poly(ethylene glycol), poly(ethylene oxide), polypropylene glycol), poly(vinyl alcohol), poly(hydroxyethyl methacrylate), poly(vinylpyrrolidone), polyacrylic acid, poly(ethyloxazoline), and poly(dimethyl acrylamide). These polymers can be copolymerized or blended with one or both of hydrophobic polymers and monomers. Additional polymers that are insoluble in water and non-biodegradable include, without limitation, silicone; silicone blends; silicone co-polymers including, without limitation, hydrophilic monomers of pHEMA, polyethylene glycol, polyvinylpyrrolidone, and glycerol; silicone hydrogel polymers such as, for example, those described in U.S. Pat. Nos. 5,962,548, 6,020,445, 6,099,852, 6,367,929, and 6,822,016, incorporated herein in their entireties by reference; phosolipids including, without limitation, phosphoryl choline derivatives; polysulfobetains; polysaccharides and carbohydrates including, without limitation, hyaluronic acid, dextran, hydroxyethyl cellulose, hydroxyl propyl cellulose, gellan gum, guar gum, heparan sulfate, chondritin sulfate, and heparin; proteins including, without limitation, albumin and ovalbumin; polyamino acids; fluorinated polymers including, without limitation, PTFE, PVDF, and teflon; polypropylene; polyethylene; nylon; and EVA. Additional examples of suitable polymers that are either or both insoluble in water and non-biodegradable include, without limitation, silicones, polyurethanes, cyanoacrylates, and polyacrylic acid.

The punctal plugs described herein can be used to deliver various active agents for the one or more of the treatment, inhibition, and prevention of numerous diseases, allergies and disorders. Each punctal plug can be used to deliver at least one active agent and can be used to deliver different types of active agents. For example, the punctal plugs can be used to deliver alcaftadine, azelastine HCl, emadastine difumerate, epinastine HCl, ketotifen fumerate, levocabastine HCl, olopatadine HCl, pheniramine maleate, and antazoline phosphate for one or more of the treatment, inhibition, and prevention of allergies. The punctal plugs can be used to deliver mast cell stabilizers, such as, for example, cromolyn sodium, lodoxamide tromethamine, nedocromil sodium, and permirolast potassium.

After the plugs is filled with the active agent, the plug is sterilized by any convenient method including, without limitation, ethylene oxide, autoclaving, irradiation, and the like and combination thereof. Preferably, sterilization is carried out through gamma radiation or use of ethylene oxide.

The punctal plugs can be used to deliver mydriatics and cycloplegics including, without limitation, atropine sulfate, homatropine, scopolamine HBr, cyclopentolate HCl, tropicamide, and phenylephrine HCl. The punctal plugs can be used to deliver ophthalmic dyes including, without limitation, rose begal, lissamine green, indocyanine green, fluorexon, and fluorescein.

The punctal plugs can be used to deliver corticosteroids including, without limitation, dexamethasone sodium phosphate, dexamethasone, fluorometholone, fluorometholone acetate, loteprednol etabonate, prednisolone acetate, prednisolone sodium phosphate, medrysone, rimexolone, and fluocinolone acetonide. The punctal plugs can be used to deliver non-steroidal anti-inflammatory agents including, without limitation, flurbiprofen sodium, suprofen, diclofenac sodium, ketorolac tromethamine, cyclosporine, rapamycin methotrexate, azathioprine, and bromocriptine.

The punctal plugs can be used to deliver anti-infective agents including, without limitation, tobramycin, moxifloxacin, ofloxacin, gatifloxacin, ciprofloxacin, gentamicin, sulfisoxazolone diolamine, sodium sulfacetamide, neomycin, propanidine, chlorhexadine, PHMB, vancomycin, polymyxin B, amikacin, norfloxacin, levofloxacin, sulfisoxazole diolamine, sodium sulfacetamide tetracycline, doxycycline, dicloxacillin, cephalexin, amoxicillin/clavulante, ceftriaxone, cefixime, erythromycin, ofloxacin, azithromycin, gentamycin, sulfadiazine, and pyrimethamine.

The punctal plugs can be used to deliver agents for the one or more of the treatment, inhibition, and prevention of glaucoma including, without limitation, epinephrines, including, for example: dipivefrin; alpha-2 adrenergic receptors, including, for example, aproclonidine and brimonidine; betablockers including, without limitation, betaxolol, carteolol, levobunolol, metipranolol, and timolol; direct miotics, including, for example, carbachol and pilocarpine; cholinesterase inhibitors, including, without limitation, physostigmine and echothiophate; carbonic anhydrase inhibitors, including, for example, acetazolamide, brinzolamide, dorzolamide, and methazolamide; prostoglandins and prostamides including, without limitation, latanoprost, bimatoprost, uravoprost, and unoprostone cidofovir.

The punctal plugs can be used to deliver antiviral agents, including, without limitation, fomivirsen sodium, foscarnet sodium, ganciclovir sodium, valciclovir HCl, trifluridine, acyclovir, and famciclovir. The punctal plugs can be used to deliver local anesthetics, including, without limitation, tetracaine HCl, proparacaine HCl, proparacaine HCl and fluorescein sodium, benoxinate and fluorescein sodium, and benoxnate and fluorexon disodium. The punctal plugs can be used to deliver antifungal agents, including, for example, fluconazole, flucytosine, amphotericin B, itraconazole, natamycin and ketocaonazole.

The punctal plugs can be used to deliver analgesics including, without limitation, acetaminophen and codeine, acetaminophen and hydrocodone, acetaminophen, ketorolac, ibuprofen, and tramadol. The punctal plugs can be used to deliver vasoconstricors including, without limitation, ephedrine hydrochloride, naphazoline hydrochloride, phenylephrine hydrochloride, tetrahydrozoline hydrochloride, and oxymetazoline. Finally, the punctal plugs can be used to deliver vitamins, antioxidants, and nutraceuticals including, without limitation, vitamins A, D, and E, lutein, taurine, glutathione, zeaxanthin, fatty acids and the like.

The active agents delivered by the punctal plugs can be formulated to contain excipients including, without limitation, synthetic and natural polymers, including, for example, polyvinylalcohol, polyethyleneglycol, PAA (polyacrylic acid), hydroxymethyl cellulose, glycerine, hypromelos, polyvinylpyrrolidone, carbopol, propyleneglycol, hydroxypropyl guar, glucam-20, hydroxypropyl cellulose, sorbitol, dextrose, polysorbate, mannitol, dextran, modified polysaccharides and gums, phosolipids, and sulphobetains.

The invention will be clarified further by consideration of the following, non-limiting examples.

EXAMPLES

Example 1

0.35 to 0.75 mg of a 2 part silicone rubber mixture with crosslinkers and catalyst obtained from Wacker Silicones, Adrian, Mich., were injected molded to form a punctal plug as shown in FIG. 2 The dimensions of the plug were as follows: the total length was 1.85 mm, the length of body 1.00 mm, diameter or radius of both the flange and arrowhead was 1.2 mm, the amount of offset from central axis was between 5 to 15 µm, there were between 2 to 5 threads with a bore diameter of about 0.4 mm.

Insertion and removal forces are summarized in Table 1:

TABLE 1

|  | Corky | Conehead |
|---|---|---|
| Insertion Force (N) | 0.22 | 0.18 |
| Time (sec) | 8 | 9 |
| Removal Force (N) | 0.17 | 0.12 |
| Time (sec) | 14 | 17 |

We claim:

1. A drug eluting punctal plug, the punctal plug comprising:
    a substantially cylindrical body having a first and a second end;
    a collarette arrangement attached to the first end of the substantially cylindrical body, the collarette having at least one opening therein, the collarette arrangement being concentrically mounted on the substantially cylindrical body;
    an anchor arrangement attached to the second end of the substantially cylindrical body, the anchor arrangement including a cone section with an apex directed away from the substantially cylindrical body and a washer portion mounted on the cone section opposite the apex, the anchor arrangement being non-concentrically mounted on the substantially cylindrical body such that the anchor arrangement and the collarette arrangement are offset from one another; and
    a reservoir containing an active agent-containing material secured therein, the reservoir positioned within at least a portion of the substantially cylindrical body and the anchor arrangement, the reservoir being in fluid communication with the at least one opening of the collarette and configured to only allow the active agent-containing material to pass therethrough and directly onto the eye.

* * * * *